US012616567B2

(12) United States Patent
Tai et al.

(10) Patent No.: US 12,616,567 B2
(45) Date of Patent: May 5, 2026

(54) LIQUID ACCOMMODATING INTRAOCULAR LENS WITH SUSPENDED CENTRAL LENS

(71) Applicants: California Institute of Technology, Pasadena, CA (US); University of Southern California, Los Angeles, CA (US)

(72) Inventors: Yu-Chong Tai, Pasadena, CA (US); Mark S. Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 13 days.

(21) Appl. No.: 18/508,701

(22) Filed: Nov. 14, 2023

(65) Prior Publication Data

US 2025/0127610 A1      Apr. 24, 2025

Related U.S. Application Data

(60) Provisional application No. 63/545,254, filed on Oct. 23, 2023.

(51) Int. Cl.
*A61F 2/16* (2006.01)

(52) U.S. Cl.
CPC .......... *A61F 2/1635* (2013.01); *A61F 2/1648* (2013.01); *A61F 2002/1682* (2015.04)

(58) Field of Classification Search
CPC .... A61F 2/1624; A61F 2/1629; A61F 2/1635; A61F 2/1648; A61F 2002/1682; A61F 2250/0003
See application file for complete search history.

(56) References Cited

U.S. PATENT DOCUMENTS

| 4,578,063 A | 3/1986 | Inman et al. |
| 4,666,445 A | 5/1987 | Tillay |

(Continued)

FOREIGN PATENT DOCUMENTS

| CN | 1283974 A | 2/2001 |
| CN | 105073066 A | 11/2015 |

(Continued)

OTHER PUBLICATIONS

Alfonso et al., "Prospective visual evaluation of apodized diffractive intraocular lenses," J Cataract Refract Surg, 33:1235-43, 2007.

(Continued)

*Primary Examiner* — Leslie A Lopez
(74) *Attorney, Agent, or Firm* — Mark P. Mathison

(57)          ABSTRACT

An intraocular lens (IOL) has a small, central lens suspended within a pliable housing and, when the housing is filled with liquid, is coaxially aligned with a second small lens embedded in the wall of the housing. The suspension is on a dome- or other-shaped webbing attached to an inner circumference of the wall. When filled with liquid, forces squeezing or pulling the equator of the housing, as with ciliary muscles in the eye, adjust a distance between the lenses in order to adjust focus. Optional haptics may project from points on or above and below the equator. A recess in the posterior hemisphere of the housing can keep cell growth away from an optical axis of the lens system. A third small lens can be embedded in an opposite wall of the housing and coaxially aligned with the other lenses to form a three-lens, ultra-zoom system.

14 Claims, 7 Drawing Sheets

(56) References Cited

U.S. PATENT DOCUMENTS

| | | | |
|---|---|---|---|
| 4,685,921 | A | 8/1987 | Peyman |
| 4,816,031 | A | 3/1989 | Pfoff |
| 4,822,360 | A | 4/1989 | Deacon |
| 4,888,016 | A | 12/1989 | Langerman |
| 4,995,880 | A | 2/1991 | Galib |
| 5,035,710 | A | 7/1991 | Nakada et al. |
| 5,091,121 | A | 2/1992 | Nakada et al. |
| 5,213,579 | A | 5/1993 | Yamada et al. |
| 6,197,057 | B1 | 3/2001 | Peyman et al. |
| 6,358,279 | B1 | 3/2002 | Tahi et al. |
| 7,137,994 | B2 | 11/2006 | de Juan, Jr. et al. |
| 7,326,649 | B2 | 2/2008 | Rodger et al. |
| 7,569,048 | B2 | 8/2009 | Brown |
| 7,774,931 | B2 | 8/2010 | Tai et al. |
| 7,806,929 | B2 | 10/2010 | Brown |
| 7,883,540 | B2 * | 2/2011 | Niwa .................... A61F 2/1648 623/6.37 |
| 8,715,345 | B2 | 5/2014 | DeBoer et al. |
| 8,771,347 | B2 | 7/2014 | DeBoer et al. |
| 9,427,312 | B2 | 8/2016 | DeBoer et al. |
| 11,376,116 | B2 | 7/2022 | Webb |
| 2004/0068317 | A1 | 4/2004 | Knight |
| 2005/0177169 | A1 | 8/2005 | Fisher et al. |
| 2006/0047339 | A1 | 3/2006 | Brown |
| 2006/0084949 | A1 | 4/2006 | Peyman |
| 2006/0178741 | A1 | 8/2006 | Zadno-Azizi et al. |
| 2007/0004852 | A1 | 1/2007 | Mentak |
| 2007/0016294 | A1 | 1/2007 | Greenberg et al. |
| 2007/0213818 | A1 | 9/2007 | Carroazp |
| 2009/0043384 | A1 | 2/2009 | Niwa et al. |
| 2012/0303118 | A1 | 11/2012 | DeBoer et al. |
| 2012/0310343 | A1 | 12/2012 | Van Noy |
| 2013/0053954 | A1 | 2/2013 | Rao et al. |
| 2013/0150960 | A1 | 6/2013 | DeBoer et al. |
| 2013/0317607 | A1 | 11/2013 | DeBoer et al. |
| 2014/0180403 | A1 * | 6/2014 | Silvestrini ............ A61F 2/1613 623/6.4 |
| 2016/0106534 | A1 * | 4/2016 | Deboer ................. A61F 2/1645 623/6.13 |
| 2016/0184090 | A1 | 6/2016 | Shi et al. |
| 2020/0008931 | A1 * | 1/2020 | Argento ................ A61F 2/1635 |
| 2022/0273423 | A1 | 9/2022 | Argento et al. |
| 2022/0387169 | A1 | 12/2022 | Ellis |

FOREIGN PATENT DOCUMENTS

| | | |
|---|---|---|
| CN | 105377189 A | 3/2016 |
| CN | 210019801 U | 2/2020 |
| CN | 112656544 A | 4/2021 |
| JP | 2007089810 | 4/2007 |
| JP | 2008-520310 A | 6/2008 |
| JP | 2010-540070 A | 12/2010 |
| KR | 1020160086767 A | 7/2016 |
| WO | 1999-40877 A1 | 8/1999 |
| WO | 2001-85067 A2 | 11/2001 |
| WO | 02/05015 A2 | 1/2002 |
| WO | 2005-050292 A1 | 6/2005 |
| WO | 2006/041550 A2 | 4/2006 |
| WO | 2006/074843 A1 | 7/2006 |
| WO | 2006/117208 A1 | 11/2006 |
| WO | 2009/021327 A1 | 2/2009 |
| WO | 2012-161749 A1 | 1/2012 |
| WO | 2015-073060 A1 | 5/2015 |
| WO | 2019106011 A1 | 6/2019 |
| WO | 2021116298 A1 | 6/2021 |

OTHER PUBLICATIONS

Ben-Nun, J. et al., "Feasibility and development of a high-power real accommodating intraocular lens," J Cataract Refract Surg, 31:1802-08, 2005.

Burd, H. et al., "Numerical modeling of the accommodating lens," Vision Research, 42:2235-51, 2002.

Chong, L. et al., "A self-stabilizing lens ring for 25-gauge vitrectomy surgery," Am J Ophthalmol, 143:350-351, 2007.

Cillino, S. et al., "One-year outcomes with new-generation multifocal intraocular lenses," Ophthalmology, 115:1508-16, 2008.

Cumming, J. et al., "Clinical evaluation of the Crystalens AT-45 accommodating intraocular lens: Results of the U.S. Food and Drug Administration clinical trial," J Cataract Refract Surg, 32:812-825, 2006.

Duane, A., "Normal values of the accommodation at all ages," JAMA, 59(12):1020-13, 1912.

Dubbelman, M. et al., "Change in shape of the aging human crystalline lens with accommodation," Vision Res, 45:117-132, 2005.

Findl, O. et al., "Meta-analysis of accommodating intraocular lenses," J Cataract Refract Surg, 33:522-527, 2007.

Glasser, A. et al., "Presbyopia and the optical changes in the human crystalline lens with age," Vision Research, 38(2):209-229, 1998.

Glasser, A., "Restoration of accommodation: surgical options for correction of presbyopia," Clin Exp Optom, 91(3):279-295, 2008.

Hermans, E. et al., "Development of a ciliary muscle-driven accommodating intraocular lens," J Cataract Refract Surg, 34:2133-2138, 2008.

Heys, K. et al., "Massive increase in the stiffness of the human lens nucleus with age: the basis for presbyopia?" Mol Vis, 10:956-963, 2004.

Kasthurirangan, S. et al., "MRI study of the changes in crystalline lens shape with accommodation and aging in humans," J Vis, 11(3):19, 1-16, 2011.

Kessler, J., "Experiments in refilling the lens," Arch Ophthalmol, 71:412-417, 1964.

Koretz, J. et al., "Accommodation and presbyopia in the human eye - aging of the anterior segment," Vision Research, 29(12):1685-92, 1989.

Koopmans, S.A. et al., "Accommodative lens refilling in rhesus monkeys," Invest Ophthalmol Vis Sci, 47:2976-2984, 2006.

Koopmans, S.A. et al., "Polymer refilling of presbyopic human lenses in vitro restores the ability to undergo accommodative changes," Invest Ophthalmol Vis Sci, 44(1): 250-257, 2003.

Menapace, R. et al., "Accommodating intraocular lenses: a critical review of present and future concepts," Graefe's Arch Clin Exp Ophthalmol, 245:473-489, 2007.

Nishi, O. et al., "Accommodation amplitude after lens refilling with injectable silicone by sealing the capsule with a plug in primates," Arch Ophthalmol, 116:1358-61, 1998.

Nishi, O. et al., "Amplitudes of accommodation of primate lenses refilled with two types of inflatable endocapsular balloons," Arch Ophthalmol, 111:1677-1684, 1993.

Nishi, Y. et al., "Lens refilling to restore accommodation," J Cataract Refract Surg, 35:374-382, 2009.

Ossma, I. et al., "Synchrony dual-optic accommodating intraocular lens. Part 2: Pilot clinical evaluation," J Cataract Refract Surg, 33:47-52, 2007.

Pau, H., et al., "The increasing sclerosis of the human lens with age and its relevance to accommodation and presbyopia," Graefe's Arch Clin Exp Ophthalmol, 229:294-296, 1990.

Qiao, W. et al., "Bio-inspired accommodating fluidic intraocular lens," Opt Lett, 34(20):3214-16, 2009.

Rosales, P. et al., "Crystalline lens radii of curvature from Purkinje and Scheimpflug imaging," J Vis, 6:1057-67, 2006.

Strenk, S. et al., "Age-related changes in human ciliary muscle and lens: Magnetic resonance imaging study," Invest Ophthalmol Vis Sci, 40:1162-69, 1999.

Strenk, L. et al., "The mechanism of presbyopia," Progress in Retinal and Eye Research, 24:379-393, 2005.

Von Helmholtz, H., "§12. Mechanism of Accommodation," Helmholtz's Treatise on Physiological Optics, pp. 143-172, Optical Society of America, 1924.

Weeber, H.A. et al., "Stiffness gradient in the crystalline lens," Graefe's Arch Clin Exp Ophthalmol, 245:1357-66, 2007.

Wolffsohn, J. el al., "Subjective and objective performance of the Lenstec KH-3500 "accommodative" intraocular lens," Br J Ophthalmol, 90:693-696, 2006.

(56)                          References Cited

OTHER PUBLICATIONS

Zhao, G et al., "Visual function after monocular implantation of apodized diffractive multifocal or single-piece monofocal intraocular lens: Randomized prospective comparison," J Cataract Refract Surg, 36(9):282-285, 2010.

* cited by examiner

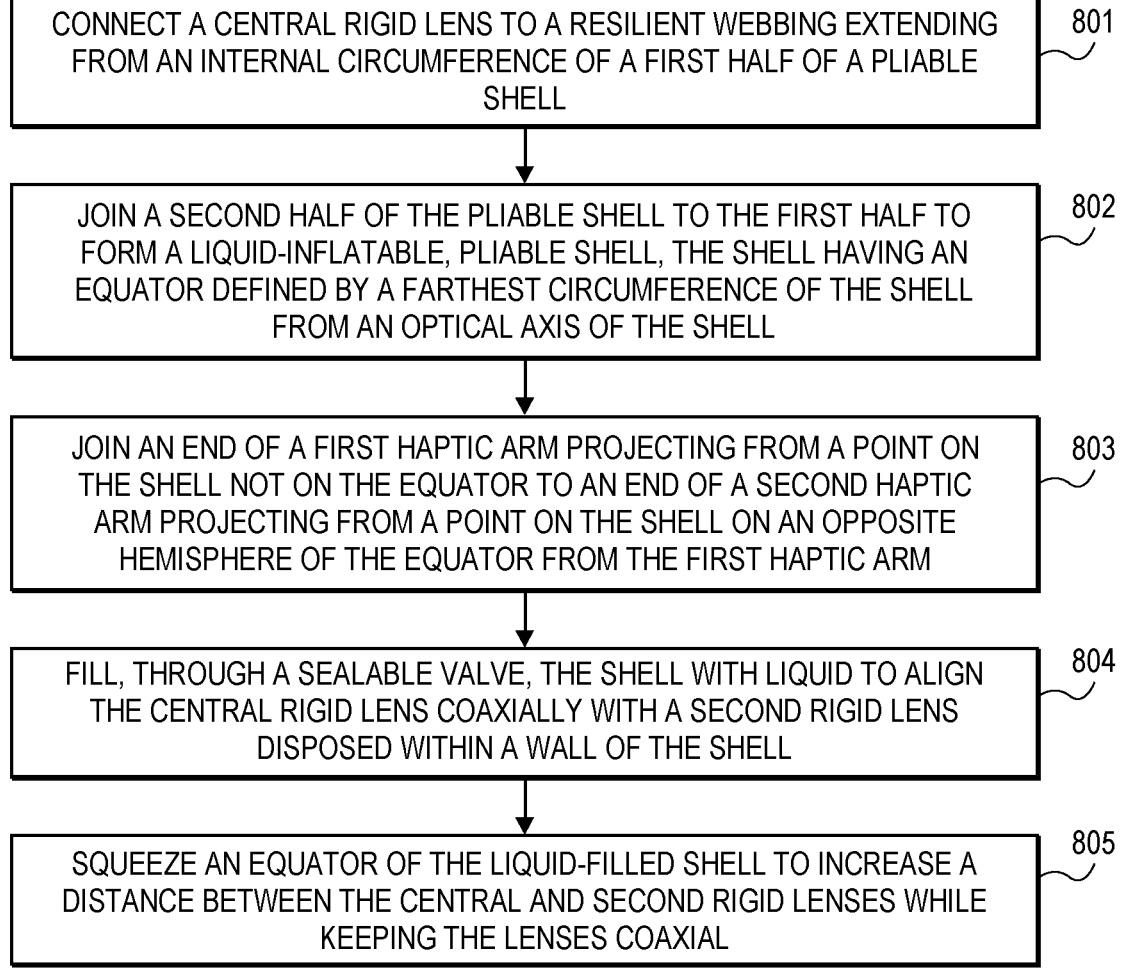

CONNECT A CENTRAL RIGID LENS TO A RESILIENT WEBBING EXTENDING FROM AN INTERNAL CIRCUMFERENCE OF A FIRST HALF OF A PLIABLE SHELL — 801

JOIN A SECOND HALF OF THE PLIABLE SHELL TO THE FIRST HALF TO FORM A LIQUID-INFLATABLE, PLIABLE SHELL, THE SHELL HAVING AN EQUATOR DEFINED BY A FARTHEST CIRCUMFERENCE OF THE SHELL FROM AN OPTICAL AXIS OF THE SHELL — 802

JOIN AN END OF A FIRST HAPTIC ARM PROJECTING FROM A POINT ON THE SHELL NOT ON THE EQUATOR TO AN END OF A SECOND HAPTIC ARM PROJECTING FROM A POINT ON THE SHELL ON AN OPPOSITE HEMISPHERE OF THE EQUATOR FROM THE FIRST HAPTIC ARM — 803

FILL, THROUGH A SEALABLE VALVE, THE SHELL WITH LIQUID TO ALIGN THE CENTRAL RIGID LENS COAXIALLY WITH A SECOND RIGID LENS DISPOSED WITHIN A WALL OF THE SHELL — 804

SQUEEZE AN EQUATOR OF THE LIQUID-FILLED SHELL TO INCREASE A DISTANCE BETWEEN THE CENTRAL AND SECOND RIGID LENSES WHILE KEEPING THE LENSES COAXIAL — 805

FIG. 8

LIQUID ACCOMMODATING INTRAOCULAR LENS WITH SUSPENDED CENTRAL LENS

CROSS-REFERENCES TO RELATED APPLICATIONS

This application claims the benefit of U.S. Provisional Application No. 63/545,254, filed Oct. 23, 2023, which is hereby incorporated by reference in its entirety for all purposes.

STATEMENT AS TO RIGHTS TO INVENTIONS MADE UNDER FEDERALLY SPONSORED RESEARCH AND DEVELOPMENT

Not applicable.

BACKGROUND

1. Field of the Art

The present disclosure relates to the technical field of ophthalmic medical devices, and more particularly, to a liquid accommodating intraocular lens with a lens suspended in its center aligned with one or more other lenses embedded in its wall.

2. Description of the Related Art

Cataract extraction combined with intraocular lens (IOL) implantation remains one of the only effective treatments for cataracts now and for some time to come. Although the implantation of a traditional monofocal intraocular lens after cataract surgery can obtain good distance vision, a monofocal intraocular lens does not have the ability to adjust focus. Patients generally have farsightedness after surgery and need to rely on glasses to meet the requirements of different close-range work.

Multifocal intraocular lens adopts a unique optical design that can simultaneously form two or more focal points in the eye. After surgery, patients can adjust the pupil size and choose different focal points to meet the needs of far-sightedness and near-sightedness, which reduces the rate of wearing glasses after surgery for cataract patients. But when there are multiple focal points, they will produce halos, glare and other shortcomings for patients.

In recent years, some scholars have tried to design adjustable intraocular lenses by changing the filling amount of the optical fluid medium (e.g., silicone oil) in the capsular bag or changing the type of optical fluid medium.

There is a need in the art for improved intraocular lenses that can be adjusted, preferably, by a patient's own ciliary eye muscles.

BRIEF SUMMARY

Generally described is a liquid-inflatable intraocular lens device resembling a soft-sided bag that has multiple precise, rigid optical lenses within it, one lens being suspended in its center by webbing. The other optical lens or lenses are on the bag walls and coaxially aligned with the central lens. When the soft-sided bag is squeezed or pulled around its perimeter, such as by the eye's ciliary muscles, the lenses move axially with respect to each other, changing the device's diopter.

The device can be made from two halves that are joined together, and the seam is not at the equator. Haptic arms can project out from the equator or from areas flanking, but not on, the equator.

Because the webbing and central lens somewhat divide the device internally in half, the device can be considered as having two chambers: an anterior chamber and a posterior chamber. The double chamber device can adjust the optical path of the overall intraocular lens device so that an adequate change in focus can be achieved.

Some embodiments of the invention are related to an accommodating intraocular lens apparatus including a liquid-inflatable, pliable shell having an equator defined by a farthest circumference of the shell from an optical axis of the shell, a sealable valve in the shell, a resilient webbing extending from an internal circumference of the shell, a central lens suspended across a center of the shell by the webbing, and a second lens disposed within a wall of the shell, wherein when the shell is full of liquid the central lens and the second lens are coaxial, and radially pulling or pushing on the equator alters a distance between the lenses while keeping the lenses coaxial.

The resilient webbing can arc in a direction parallel to the optical axis, like a dome. The resilient webbing can include multiple distinct curved arms or it can include a film annulus having apertures therein. A seam can be formed from two halves of the pliable shell, wherein the seam neither is disposed at nor crosses the equator. A depression can be formed in the shell, the depression having a continuous rim disposed around the optical axis, the continuous rim configured to seal against an enveloping capsular bag when implanted. A highest point within the depression can be lower than the continuous rim when the shell is full of liquid, the depression being configured to hold an enveloping capsular bag away from shell wall material within the depression.

A third lens can be disposed within a wall of the shell opposite the second lens, wherein when the shell is full of liquid, radially pulling or pushing on the equator alters a distance between the central lens and third lens while keeping the first, second, and third lenses coaxial.

The apparatus can further include a set of haptic arms projecting from areas on the shell on or not on the equator of the shell. The set of haptic arms can be called a first set of haptic arms, the apparatus further including a second set of haptic arms projecting from areas on the shell on an opposite hemisphere of the equator from the first set of haptic arms. Ends of the first and second haptic arms can be joined together.

The sealable valve can include an annulus and a self-sealing polymer body surrounded by the annulus, the polymer body being softer than the annulus. A layer of parylene can be laid over the sealable valve. The central lens or other lens(es) can be formed from polymethyl methacrylate (PMMA), silicone, siloxane, fluorosilane, or hydrophobic acrylate. Liquid, such as silicone oil, can fill the liquid-inflatable, pliable shell.

Some embodiments are related to a method of manufacturing and testing an accommodating intraocular lens, the method including connecting a central lens to a resilient webbing extending from an internal circumference of a first half of a pliable shell, joining a second half of the pliable shell to the first half to form a liquid-inflatable, pliable shell, the shell having an equator defined by a farthest circumference of the shell from an optical axis of the shell, filling, through a sealable valve, the shell with liquid to align the central lens coaxially with a second lens disposed within a wall of the shell, and squeezing an equator of the liquid-filled shell to increase a distance between the central and second lenses while keeping the lenses coaxial.

The joining can include adding uncured polymer across the halves to form a seam, wherein the seam neither is disposed at nor crosses the equator. The method can further include joining an end of a first haptic arm projecting from a point on the shell not on the equator to an end of a second haptic arm projecting from a point on the shell on an opposite hemisphere of the equator from the first haptic arm. It can further include folding or rolling the shell to prepare for implantation.

Some embodiments are related to a liquid accommodating intraocular lens with double chambers, including a capsule, in which a chamber is formed, the capsule including an anterior capsule and a posterior capsule, the anterior capsule and the posterior capsule being fluidically connected, a sealing valve disposed on the capsule, a film layer disposed in the chamber to divide the chamber into an anterior chamber and a posterior chamber, the anterior chamber and the posterior chamber being fluidically connected, and a central optical lens with a preset power formed on the film layer, wherein the central optical lens is formed in a middle of the film layer

BRIEF DESCRIPTION OF THE DRAWINGS

FIG. 8 is a flowchart illustrating a process in accordance with an embodiment.

DETAILED DESCRIPTION

An accommodating intraocular lens device is described with multiple smaller lenses inside that can move with respect to each other in response to a patient's ciliary muscles contracting or expanding. A central lens is suspended in the middle of the device from a dome-like thin webbing that keeps its tension and shape. The central lens and other lens(es) are coaxially aligned with one another, at least when liquid fills the device, and stay axially aligned, more or less, when moved.

"Bisect" includes dividing into two sections, or as otherwise known in the art. The two sections are not necessarily equal parts.

A "half" of a device is a portion of the device when it is divided into or comes from two parts, or as otherwise known in the art. A half is not necessarily anywhere near an exact half of an object but rather is a substantial portion of the device.

"Circumference" of a 3-dimensional object includes a circumference of a circle, oval, or other closed-form shape around a central axis as seen from a cross section view of the object, or as otherwise known in the art. It does not necessarily mean the largest circumference of the object.

"Equator" of a 3-dimensional object includes a largest circumference of an object, or as otherwise known in the art.

Figure 1:
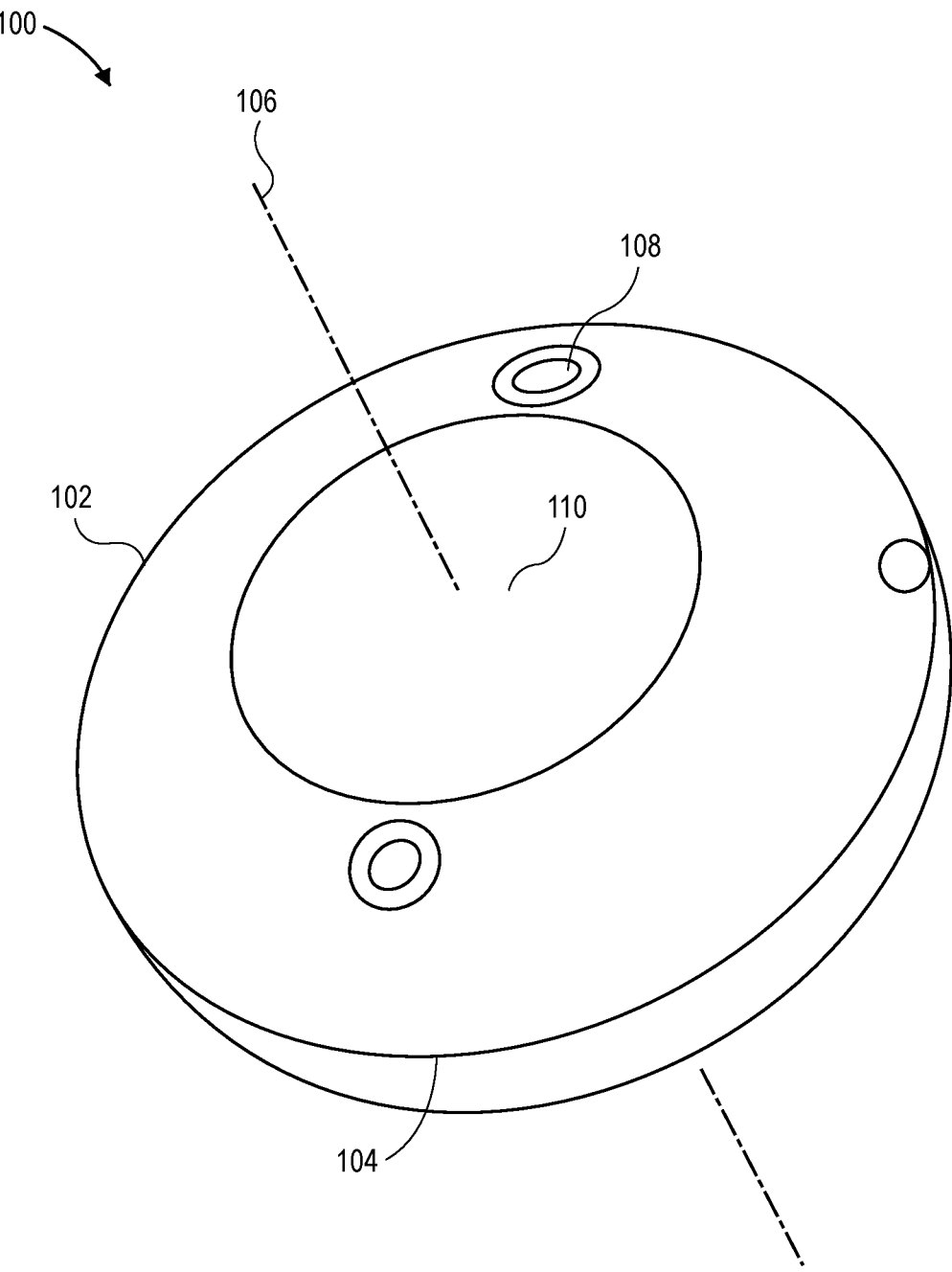
FIG. 1 is a perspective view of an accommodating intraocular lens device without haptics in accordance with an embodiment.

FIG. 1 is a perspective view of accommodating intraocular lens device 100. It is composed of liquid-inflatable shell 102, which is made of a pliable polymer such a silicone, and as shown is fully inflated with liquid silicone. The shell, or capsule, is circular around optical axis 106 and has equator 104 defined by the farthest outer circumference from the optical axis.

Sealable valve 108, sometimes referred to as a sealing valve, is disposed on the mostly visible anterior half of the device. This affords access by an ophthalmologist to fill or adjust. Shown on an opposite side of the axis, but on the same hemisphere, is a second sealable valve.

Also visible on the anterior half is second lens 110, which is mounted in the wall of the shell. Second lens 110 is a precisely made rigid lens with a preset power.

Figure 2:
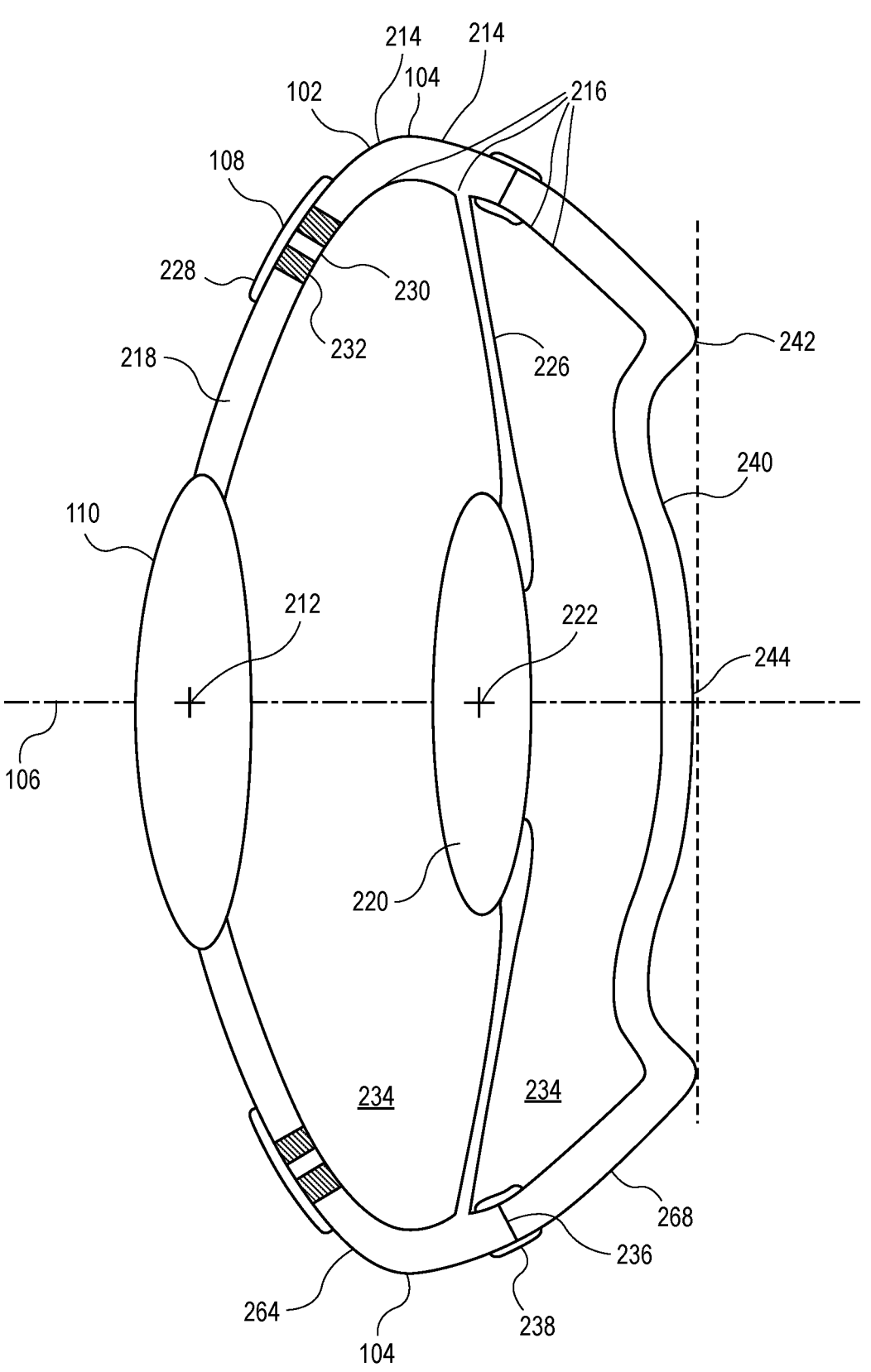
FIG. 2 is a cross section view of a two-lens intraocular lens device in accordance with an embodiment.

FIG. 2 is a cross section view of the intraocular lens device of FIG. 1. In shell 102, second lens 110 that was visible in FIG. 1 is embedded in pliable wall 218. Wall 218 wraps around the entire device. Outer circumferences 214 of the wall are outside of the device, the largest labeled as device equator 104. Meanwhile, inner circumferences 216 are on the inside of wall 218 facing filling liquid 234.

Liquid 234 was injected through sealable valve 108. Sealable valve 108 includes hard-polymer annulus 232, sometimes referred to as a ring body, disposed on the anterior half 264. Annulus 232 surrounds self-sealing polymer body 230, the Shore hardness of the body being less than that of the annulus.

The valve body is preferably round and the annulus is preferably a ring. When injecting optical fluid medium from the sealable valve 108, due to the smaller hardness of body than the surrounding annulus it is locally suitable for the injection needle to enter capsule 102. Also with the soft body, it is easier to achieve sealing after the injection needle is withdrawn to prevent the leakage of the optical fluid medium. The annulus can be made of hard silicone, and the valve body made of soft silicone.

Parylene layer 228 covers the outer surface of the sealable valve 108 and also partially overlaps the outer surface of the capsule 102. This overlap increases the contact area of the parylene layer 228 and sealable valve 108 for adhesion and helps avoid a potential concentration of stress at the interface of the sealable valve 108 and the capsule 102.

The Young's modulus and hardness of parylene layer 228 are significantly higher than sealable valve 108, and the adhesion between parylene layer 228 and sealable valve 108 is better, which is equivalent to making a layer of reinforced baffle outside the sealing valve. Therefore, when an injection needle is withdrawn, the optical fluid medium (such as silicone oil) in the sealing valve can generate outward pressure on the sealing valve, and the outward pressure can make the sealing valve self-close under the protection of the rigid parylene layer, so that it can play a role in sealing and leakage prevention for a long term.

On the exemplary embodiment in the figure, there are two sealable valves 108 symmetrically disposed on the central axis of the capsule 102. One of the sealable valves can be used for injection, and the other sealable valve plays a role in mechanical compensation and balancing, and can also be used as a spare valve. Other numbers of sealable valves may be used.

The optical fluid medium 234 can be silicone oil, silicomethane, sterile heavy water for ophthalmology (perfluorodecalin C10F18), sodium hyaluronate (healon GV), or other liquids. The shell can be prefilled as well. During the surgery, the liquid can be adjusted until the set shape or optical path is met.

Resilient webbing 226 extends from an internal circumference 216 of pliable shell 102 to suspend central lens 220. Webbing 226 arcs slightly in the direction parallel to optical axis 106, a product of the three-dimensional dome shape of the webbing. Central lens 220 is coaxially aligned with second lens 110.

Second lens 110 has lens center 212, and central lens 220 has lens center 222. When forces push radially (up and down in the figure) on equator 104 or other outer circumferences 214 of shell 102, they are transferred through the inflated structure to alter the distance between lens centers 212 and 222 while keeping lenses 110 and 220 coaxial. As a result, the lenses change their ultimate focus point and zoom.

During manufacture, shell 102 was combined from two halves, anterior half 264 and posterior half 268. The halves are joined at seam 236. Seam 236 runs all of the way around shell 102 but is neither disposed at nor crosses equator 104. Further, polymer 238 that was added to seal and form the seam, now cured, neither is disposed at nor crosses equator 104. Avoiding the equator with the somewhat thicker seam allows the equator to more consistently carry and transfer stresses that move the lenses with respect to each other.

Circular depression 240 is formed in posterior half 268 of shell 102. Depression 240 has continuous rim 242 surrounding it and optical axis 106. Continuous rim 242 avoids localized notches or other features so that the rim can seal against an enveloping capsular bag when shell 102 is implanted within a subject.

A technical advantage of the seal is that it helps prevent cells from growing and migrating over time along the shell from outer regions to the middle where they can occlude vision around the optical axis.

Continuous rim 242 is higher than highest point 244 within depression 240 as shown in the figure. That is, any line from rim to rim does not touch any portion of the depression within the rim. This configuration holds the enveloping capsular bag away from the wall 218 of shell 102.

A technical advantage of holding the wall away from the capsular bag is so that a surgical laser may be used to delicately cut a posterior portion of the capsular bag without its localized heat on the capsular bag melting the side of the shell.

Figures 3A, 3B, 3C:
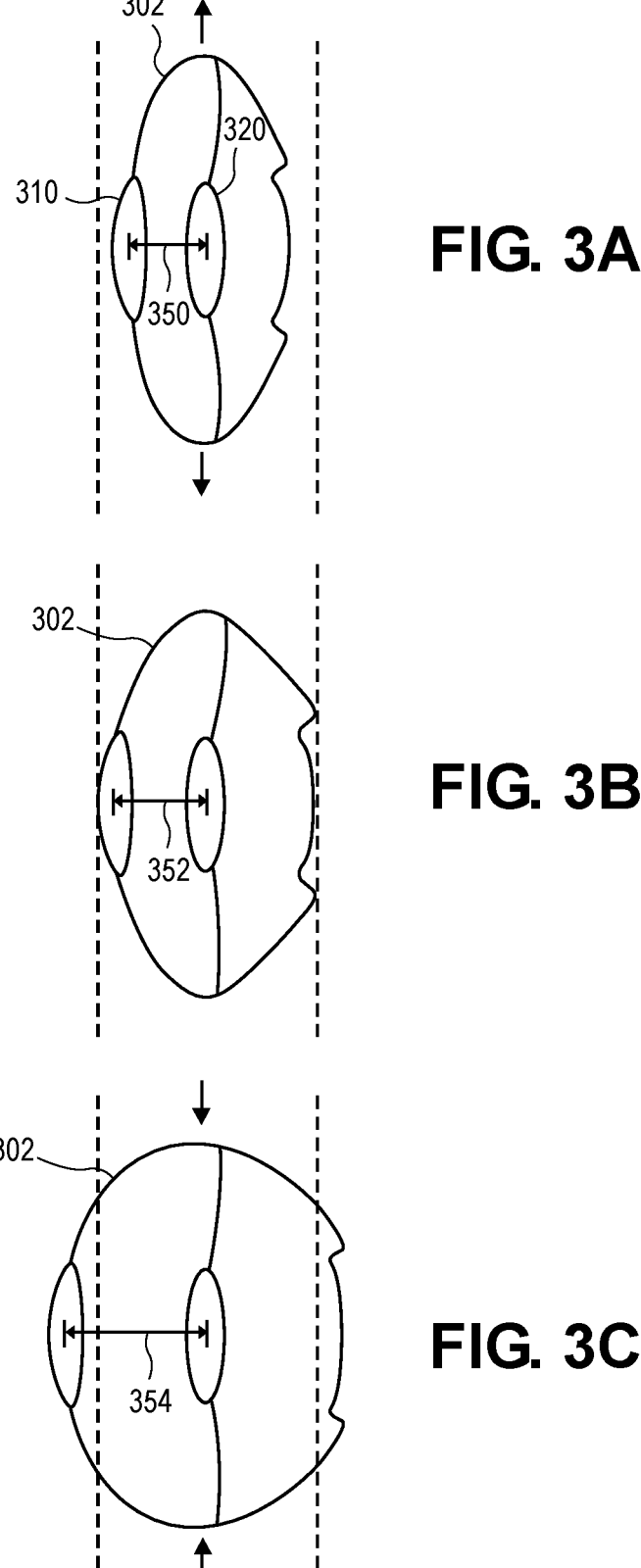
FIG. 3A is a cross section view of a device being pulled at its equator in accordance with an embodiment.
FIG. 3B is a cross section view of the device of FIG. 3A at rest in accordance with an embodiment.
FIG. 3C is a cross section view of the device of FIG. 3A being squeezed at its equator in accordance with an embodiment.

FIGS. 3A-3C are cross section views of a liquid-filled intraocular device with shell 302. Mounted in the wall of shell 302 is second lens 310. Suspended within shell 302 is central lens 320. Distances between the lenses' respective centers is shown in the figures.

In FIG. 3A, the equator is pulled, either by ciliary muscles or a test fixture, resulting in a relatively short distance 350 between the lens centers.

In FIG. 3B the shell is at rest with no pulling or pushing forces on its equator, resulting in a longer, "at rest" distance 352 between the lens centers.

In FIG. 3C, the equator is squeezed, resulting in a relatively long distance 354 between lens centers.

The design allows the same application of radial forces that affects focus in a natural lens also to affect the focus in this multi-miniature lens device. If calibrated correctly, in some cases a patient may not even need glasses. The central lens, suspended on a dome-shaped webbing can cause the correct movement of the lenses within and change their focus.

Figure 4:
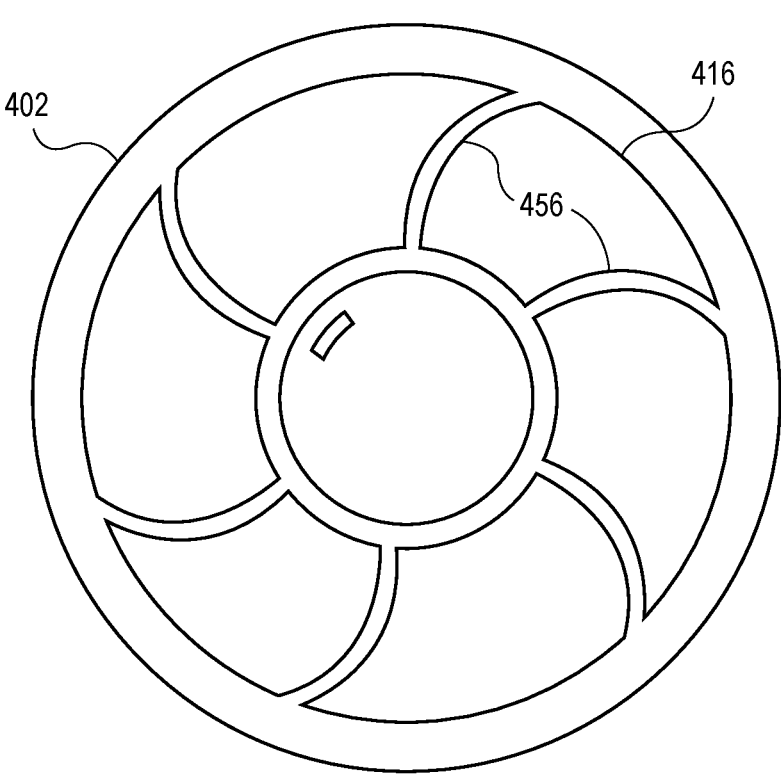
FIG. 4 is a radial cross section of a device showing webbing with multiple distinct curved arms in accordance with an embodiment.
Figure 5:
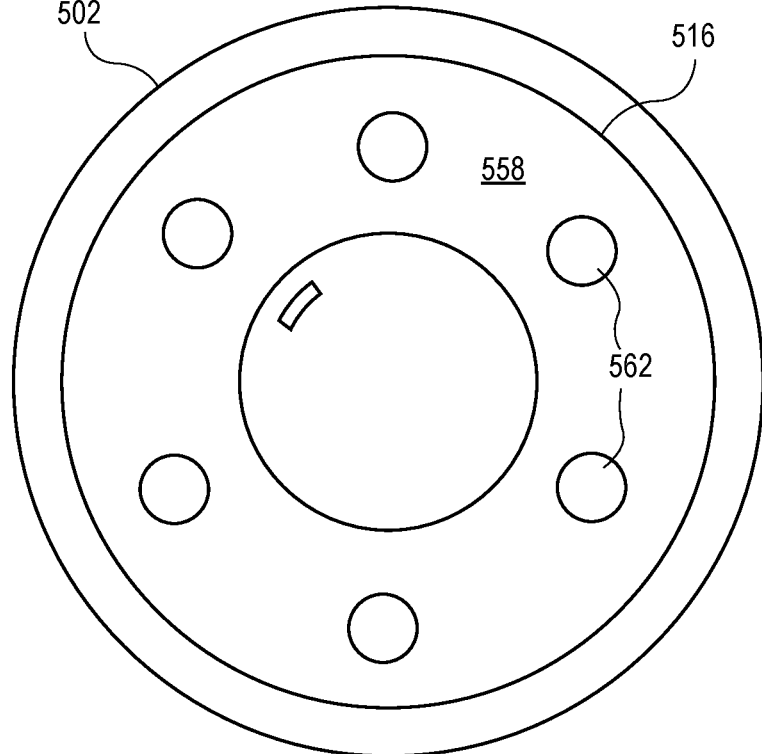
FIG. 5 is a radial cross section of a device showing webbing that is an annulus of film having holes in accordance with an embodiment.

FIGS. 4 and 5 show different types of webbing that can be employed to suspend a central lens.

In FIG. 4, multiple distinct curved arms 456 extend from inner circumference 416 of shell 402. These arms may be calibrated to be relatively thick compared to wider arms or a more continuous dome of material.

In FIG. 5, an annulus of film 558 with holes 562 extends from inner circumference 516 of shell 502. Film 558 is a thin film layer that may or may not be separately created from the rest of the half. The thickness of the film and/or sizes of the holes may be calibrated to move the central lens more or less depending on radial forces projected onto the outer perimeter.

Figure 6:
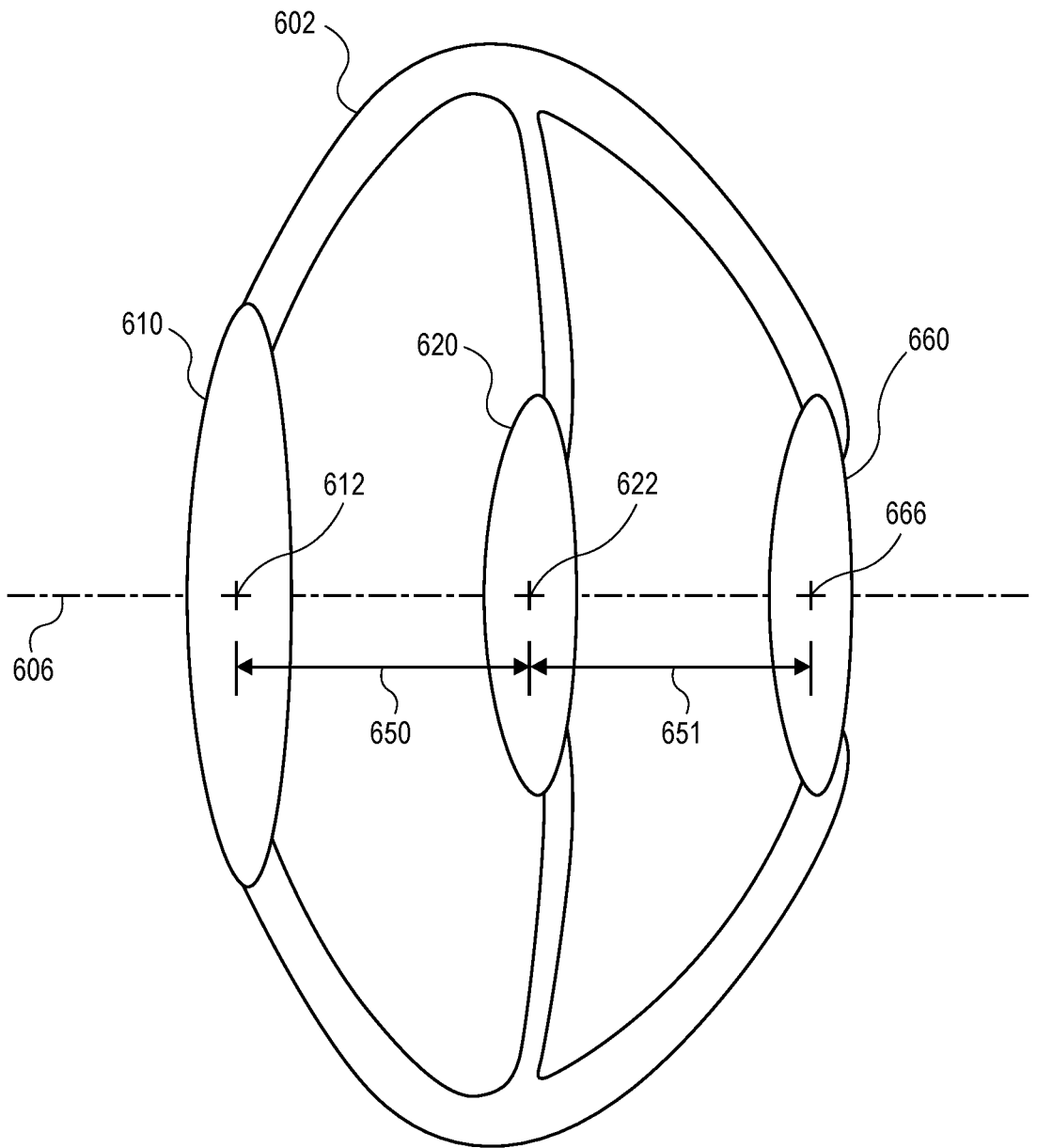
FIG. 6 is a cross section view of a three-lens intraocular lens device in accordance with an embodiment.

FIG. 6 is a cross section view of a three-lens intraocular lens device. Pliable shell 602 encapsulates central lens 620, suspended on a webbing inside. Central lens 620 has lens center 622. Second lens 610 is embedded in its anterior half and has lens center 612.

Third lens 660 is disposed within the wall of shell 602 on an opposite hemisphere from the second lens. Because the second lens is embedded in the anterior half, the third lens is embedded in the posterior half. Third lens 660 has lens center 666.

When shell 602 is full of liquid, central lens 620, second lens 610, and third lens 660 are coaxially aligned along optical axis 606 of shell 602. Radially pulling or pushing on the equator of shell 602 alters distance 650 between central lens 620 and second lens 610. It can also alter distance 651 between central lens 620 and third lens 660. Distances 650 and 651 change all while keeping the lenses coaxially aligned.

A technical advantage of a triple lens system is that higher optical powers can be obtained. Also, there may be more ways and adjusting means to calibrate the lenses. This is especially advantageous for subjects whose ciliary muscles or other natural eye components are compromised.

Figure 7A:
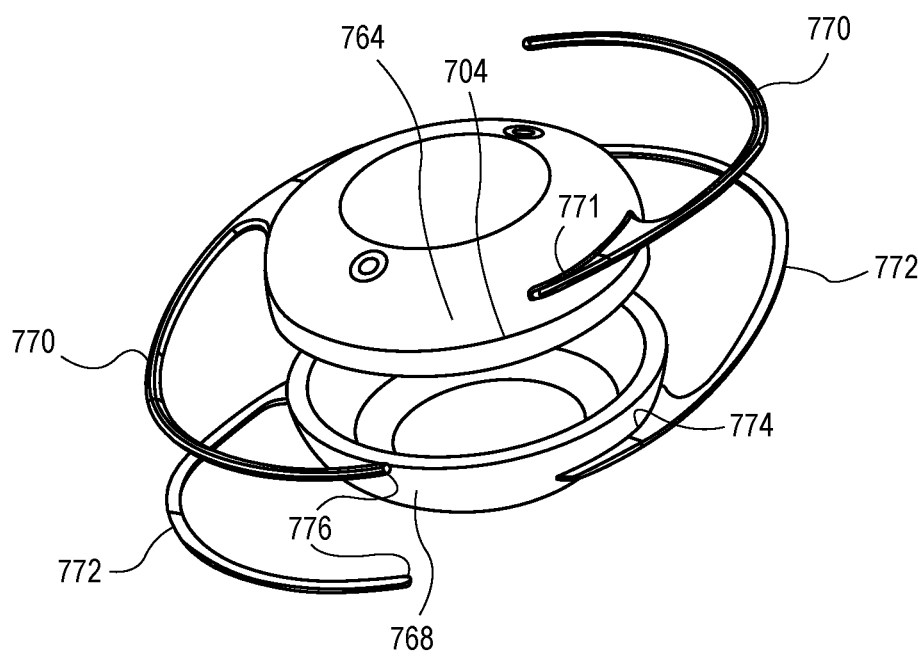
FIG. 7A is a perspective exploded view of two halves of a device, the anterior and posterior capsules, with haptics in accordance with an embodiment.
Figure 7B:
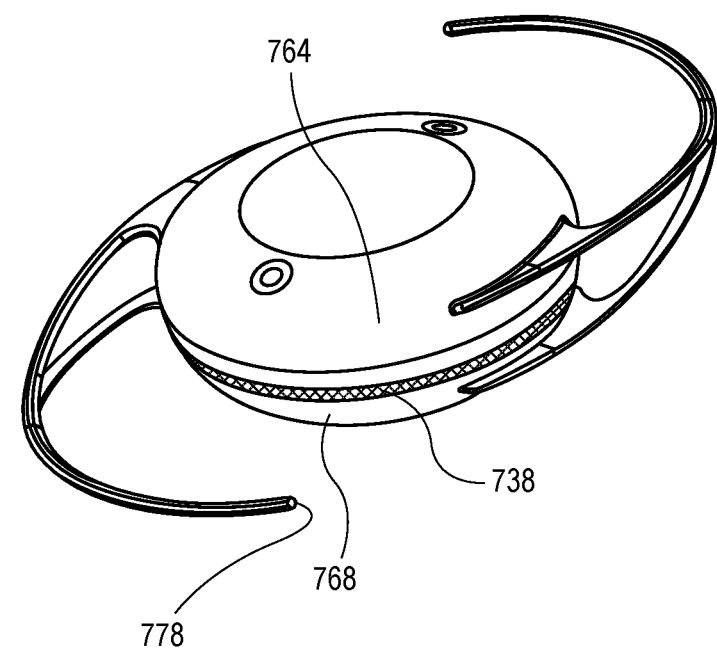
FIG. 7B is a perspective view of the two joined halves of the device of FIG. 7A.

FIGS. 7A-7B are perspective views of a device with haptics 770 and 772 stemming from anterior half 764 and posterior half 768, respectively. As with haptics in other ocular devices, the haptics support the device in the lens capsule that is associating with the action of the ciliary muscle, adjusting the shape of the capsule. The haptics can also be sutured directly into the eye wall where the ciliary body is and can be used either where there is no capsular bag or a compromised capsular bag. Haptics can be made of polyvinylidene fluoride (PVDF), polymethyl methacrylate (PMMA), polyimide, acrylate, or other resilient biocompatible materials.

FIG. 7A illustrates halves prior to joining, with anterior portion 764 having the largest width circumference, equator 704. At point 771 on anterior portion 764, a haptic anterior connecting arm 770 is connected to its outer surface. The point is about halfway between the seam and a pole of hemispherical half 764, i.e., at one half the thickness of anterior half 764. A second connecting arm 770, of the same set of haptic arms, is disposed on an opposite side on the same hemisphere.

Similarly, on posterior half 768 a haptic anterior connecting arm 772 is connected at point 774 to the posterior half's outer surface. Point 774 is about halfway between the seam and a pole of hemispherical half 768, i.e., at one half the thickness of posterior half 768. A second connecting arm 772, of the same second set of haptic arms, is disposed on an opposite side on the same hemisphere.

At this point, ends 776 of haptic arms 770 and 772 are free. When the two hemispheres, anterior half 764 and posterior half 768, are joined together, the haptic arms may remain free. Or each haptic arm may be mated to its respective arm on the opposite hemisphere.

FIG. 7B illustrates anterior half 764 and posterior half 768 joined together at seam 738. In this exemplary embodiment, the ends of the haptic arms are angled and joined together to form Y-shaped structures with joined ends 778. They can be bonded with a glue such as silicone.

At technical advantage of this configuration, with the front connecting arms joined at their ends to the rear connecting arms, is that the arms avoid seam 738 between the halves and avoid equator 704. It has been demonstrated by mechanical simulation analysis and experiments that an optimal force position can be found for the connection position of the haptics. The split Y design can facilitate the force balance of the capsule in refractive adjustment. It can also achieve controllable deformation, thereby increasing the accuracy and effectiveness of refractive adjustment.

FIG. 8 is a flowchart illustrating process 800 in accordance with an embodiment. In operation 801, a central rigid lens is connected to a resilient webbing extending from an internal circumference of a first half of a pliable shell. In operation 802, a second half of the pliable shell is joined to the first half to form a liquid-inflatable, pliable shell, the shell having an equator defined by a farthest circumference of the shell from an optical axis of the shell. In operation 803, an end of a first haptic arm projecting from a point on the shell not on the equator is joined to an end of a second haptic arm projecting from a point on the shell on an opposite hemisphere of the equator from the first haptic arm. In operation 804, the shell is filled with liquid, through a sealable valve, to align the central rigid lens coaxially with a second rigid lens disposed within a wall of the shell. In operation 805, an equator of the liquid-filled shell is squeezed to increase a distance between the central and second rigid lenses while keeping the lenses coaxial. This can be done in testing or during or after implantation.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. An accommodating intraocular lens apparatus comprising:
   a liquid-inflatable, pliable shell having an equator defined by a farthest circumference of the shell from an optical axis of the shell;
   a sealable valve in the shell;
   a resilient webbing extending from an internal circumference of the shell;
   a central lens suspended across a center of the shell by the webbing;
   a second lens disposed within an anterior wall of the shell; and
   a depression formed in a posterior wall of the shell opposite the second lens, the depression having a continuous rim disposed around the optical axis,
   wherein when the shell is full of liquid:
      a most posterior point within the depression is less posterior than the entire rim such that any line between any two points on the rim does not touch any portion of the depression, the central lens and the second lens are coaxial, and radially pulling or pushing on the equator alters a distance between the lenses while keeping the lenses coaxial.

2. The apparatus of claim 1 wherein the resilient webbing arcs in a direction parallel to the optical axis.

3. The apparatus of claim 1 wherein the resilient webbing includes multiple distinct curved arms.

4. The apparatus of claim 1 wherein the resilient webbing includes a film annulus having apertures therein.

5. The apparatus of claim 1 further comprising:

a seam formed from two halves of the pliable shell, wherein the seam neither is disposed at nor crosses the equator.

6. The apparatus of claim 1 further comprising:

a set of haptic arms projecting from areas on the shell not on the equator of the shell.

7. The apparatus of claim 6 wherein the set of haptic arms is a first set of haptic arms, the apparatus further comprising:

a second set of haptic arms projecting from areas on the shell on an opposite hemisphere of the equator from the first set of haptic arms.

8. The apparatus of claim 7 wherein ends of the first and the second haptic arms are joined together.

9. The apparatus of claim 1 wherein the sealable valve includes:

an annulus; and a self-sealing polymer body surrounded by the annulus, the polymer body being softer than the annulus.

10. The apparatus of claim 1 further comprising:

a layer of parylene over the sealable valve.

11. The apparatus of claim 1 wherein the central lens is formed from polymethyl methacrylate (PMMA), silicone, siloxane, fluorosilane, or hydrophobic acrylate.

12. The apparatus of claim 1 further comprising:

the liquid filling the liquid-inflatable, pliable shell.

13. The apparatus of claim 5 wherein the seam was produced by:

adding uncured polymer across a first half of the pliable shell and a second half of the pliable shell in order to join the halves and form a seam.

14. The apparatus of claim 1 wherein the sealable valve is a first sealable valve, the apparatus further comprising:

a second sealable valve on the pliable shell disposed symmetrically opposite the optical axis from the first sealable valve.

* * * * *